(12) United States Patent
Amemiya

(10) Patent No.: US 9,182,377 B2
(45) Date of Patent: Nov. 10, 2015

(54) ULTRASONIC TRANSDUCER DRIVE CIRCUIT AND ULTRASONIC IMAGE DISPLAY APPARATUS

(75) Inventor: Shinichi Amemiya, Tokyo (JP)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 784 days.

(21) Appl. No.: 13/472,134

(22) Filed: May 15, 2012

(65) Prior Publication Data

US 2012/0294113 A1  Nov. 22, 2012

(30) Foreign Application Priority Data

May 16, 2011  (JP) .................................. 2011-109442

(51) Int. Cl.
| | | |
|---|---|---|
| *G03B 42/06* | (2006.01) | |
| *G01N 29/06* | (2006.01) | |
| *G01N 29/34* | (2006.01) | |
| *G01S 7/521* | (2006.01) | |
| *G01S 15/10* | (2006.01) | |
| *G01S 15/89* | (2006.01) | |
| *B06B 1/02* | (2006.01) | |
| *G01S 15/87* | (2006.01) | |
| *A61B 8/00* | (2006.01) | |

(52) U.S. Cl.
CPC .......... *G01N 29/0672* (2013.01); *B06B 1/0215* (2013.01); *G01N 29/34* (2013.01); *G01S 7/521* (2013.01); *G01S 15/102* (2013.01); *G01S 15/89* (2013.01); *A61B 8/54* (2013.01); *G01N 2291/044* (2013.01); *G01S 15/876* (2013.01)

(58) Field of Classification Search
CPC ..... B06B 1/0207; B06B 1/0215; G01N 29/34
USPC ............................................... 367/7; 310/317
See application file for complete search history.

(56) References Cited

U.S. PATENT DOCUMENTS

| | | |
|---|---|---|
| 6,759,888 B1 | 7/2004 | Wodnicki |
| 6,836,159 B2 | 12/2004 | Wodnicki |
| 6,956,426 B2 | 10/2005 | Wodnicki |

(Continued)

FOREIGN PATENT DOCUMENTS

| | | |
|---|---|---|
| JP | 2009101072 | 5/2009 |
| JP | 2010-022760 | 4/2010 |

OTHER PUBLICATIONS

Unofficial Translation of NL Search Report and Written Opinion from corresponding NL Application No. 2008826 dated May 7, 2013.

*Primary Examiner* — Mark Hellner

(57) ABSTRACT

An ultrasonic transducer drive circuit for driving an ultrasonic transducer by outputting pulses including a positive pulse and a negative pulse to an output line is provided. The ultrasonic transducer includes a positive voltage supply circuit, a negative voltage supply circuit, a current-inflow-type ground clamp circuit configured to operate when voltage in the output line is positive voltage, and a current-outflow-type ground clamp circuit configured to operate when voltage in the output line is negative voltage, wherein the current-inflow-type ground clamp circuit is configured to enter an operation state at a time of generating the negative pulse in a state where the voltage in the output line is positive voltage, and the current-outflow-type ground clamp circuit is configured to enter an operation state at a time of generating the positive pulse in a state where the voltage in the output line is negative voltage.

15 Claims, 13 Drawing Sheets

(56) References Cited

U.S. PATENT DOCUMENTS

| | | |
|---|---|---|
| 7,705,517 B1 | 4/2010 | Koen et al. |
| 7,855,609 B2 * | 12/2010 | Amemiya ............... 331/116 FE |
| 2008/0066552 A1 * | 3/2008 | Amemiya ..................... 73/602 |
| 2008/0071171 A1 | 3/2008 | Amemiya |
| 2010/0113934 A1 | 5/2010 | Oguzman et al. |
| 2010/0113935 A1 | 5/2010 | Koen et al. |
| 2010/0331703 A1 | 12/2010 | Amemiya |
| 2012/0161819 A1 * | 6/2012 | Rossi et al. ................... 327/109 |
| 2012/0170770 A1 * | 7/2012 | Lesso et al. ................... 381/107 |

* cited by examiner

US 9,182,377 B2

ULTRASONIC TRANSDUCER DRIVE CIRCUIT AND ULTRASONIC IMAGE DISPLAY APPARATUS

CROSS REFERENCE TO RELATED APPLICATIONS

This application claims the benefit of Japanese Patent Application No. 2011-109442 filed May 16, 2011, which is hereby incorporated by reference in its entirety.

BACKGROUND OF THE INVENTION

The present invention relates to an ultrasonic transducer drive circuit and an ultrasonic image display apparatus.

An ultrasonic transducer drive circuit is a circuit for driving an ultrasonic transducer by outputting pulses made by a positive voltage pulse and a negative voltage pulse to an output line of the ultrasonic transducer. As such an ultrasonic transducer drive circuit, for example, Japanese Unexamined Patent Application Publication No. 2009-101072 discloses a circuit having a positive voltage supply circuit for supplying positive voltage to the output line and a negative voltage supply circuit for supplying negative voltage to the output line. In the ultrasonic transducer drive circuit, when a negative voltage pulse is generated in a state where the voltage in the output line is positive voltage, the negative voltage supply circuit is operated and, to generate a positive voltage pulse in a state where the voltage in the output line is negative voltage, the positive voltage supply circuit is operated.

When the negative voltage supply circuit is operated at the time of generating the negative voltage pulse in a state where the voltage in the output line is positive voltage, current flows in the negative voltage supply circuit for predetermined time and power is consumed. When the positive voltage supply circuit is operated at the time of generating the positive voltage pulse in a state where the voltage in the output line is negative voltage, current flows in the positive voltage supply circuit for predetermined time and power is consumed. Therefore, suppression of power consumption in the positive voltage supply circuit and the negative voltage supply circuit is an issue.

BRIEF DESCRIPTION OF THE INVENTION

In one aspect, an ultrasonic transducer drive circuit for driving an ultrasonic transducer by outputting pulses made of a positive pulse and a negative pulse to an output line to the ultrasonic transducer is provided. The ultrasonic transducer drive circuit includes a positive voltage supply circuit for supplying positive voltage to the output line, a negative voltage supply circuit for supplying negative voltage to the output line, a current-inflow-type ground clamp circuit which operates when voltage in the output line is positive voltage, and changes the voltage in the output line to ground voltage, and a current-outflow-type ground clamp circuit which operates when voltage in the output line is negative voltage, and changes the voltage in the output line to ground voltage. The current-inflow-type ground clamp circuit enters an operation state when the negative pulse is generated in a state where the voltage in the output line is positive voltage, and the current-outflow-type ground clamp circuit enters an operation state when the positive pulse is generated in a state where the voltage in the output line is negative voltage.

Accordingly, at the time of generating a negative pulse in a state where the voltage in the output line is positive voltage, the current inflow-type ground clamp circuit operates in place of the negative voltage supply circuit. At the time of generating a positive pulse in a state where the voltage in the output line is negative voltage, the current-outflow-type ground clamp circuit operates in place of the positive voltage supply circuit. Therefore, power consumption in the positive voltage supply circuit and the negative voltage supply circuit can be suppressed.

DETAILED DESCRIPTION OF THE INVENTION

Embodiments will be described in detail below with reference to the drawings.

First Embodiment

Figure 1:
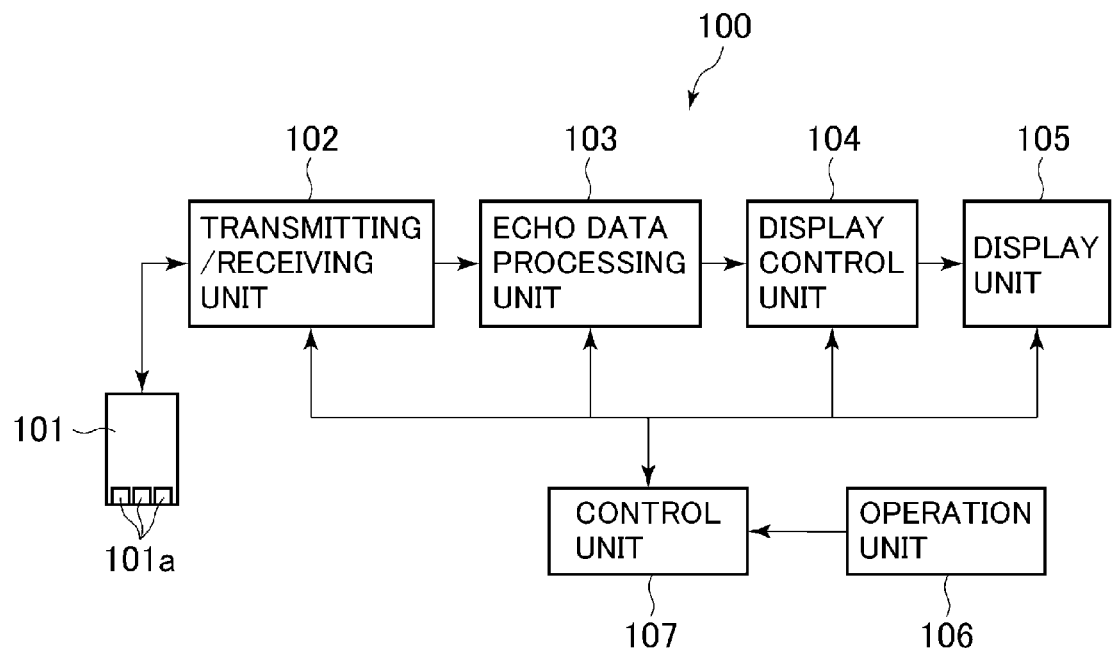
FIG. 1 is a block diagram showing an example of an embodiment of an ultrasonic image display apparatus.

First, a first embodiment will be described with reference to FIGS. 1 to 9. As illustrated in FIG. 1, an ultrasonic image display apparatus 100 has an ultrasonic probe 101, a transmitting/receiving unit 102, an echo data processing unit 103, a display control unit 104, a display unit 105, an operation unit 106, and a control unit 107.

The ultrasonic probe 101 is provided with a plurality of ultrasonic transducers 101a that transmit/receive ultrasonic waves.

Figure 2:
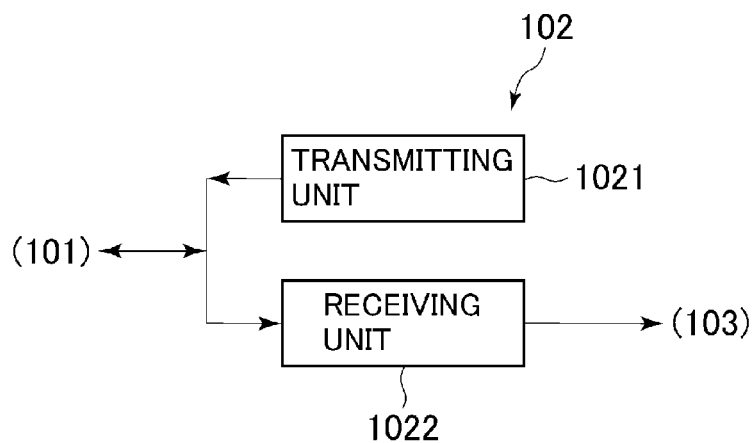
FIG. 2 is a block diagram showing a transmitting/receiving unit in the ultrasonic image display apparatus illustrated in FIG. 1.

The transmitting/receiving unit 102 has a transmitting unit 1021 and a receiving unit 1022 as illustrated in FIG. 2. The transmitting unit 1021 supplies an electric signal for transmitting ultrasonic waves under a predetermined scan condition to the ultrasonic probe 101 on the basis of a control signal from the control unit 107. The transmitting unit 1021 has an ultrasonic transducer drive circuit 1 (not shown in FIG. 2, refer to FIG. 3) which supplies an electric signal for transmitting ultrasonic waves by driving the ultrasonic transducers 101a. The ultrasonic transducer drive circuit 1 will be described later.

The receiving unit 1022 performs signal processes such as A/D conversion and phasing and adding process on an echo signal received by the ultrasonic probe 101 and outputs obtained echo data to the echo data processing unit 103.

The echo data processing unit 103 performs a process for generating an ultrasonic image on the echo data supplied from the transmitting/receiving unit 102. For example, the echo data processing unit 103 performs B-mode processes such as logarithmic compression process and envelope detecting process, Doppler processes such as orthogonal detecting process and filter process, and the like.

The display control unit 104 scan-converts the data obtained by the echo data processing unit 103 by a scan converter to generate ultrasonic image data. The display control unit 104 displays an ultrasonic image based on the ultrasonic image data on the display unit 105.

The display unit 105 is an LCD (Liquid Crystal Display), a CRT (Cathode Ray Tube), or the like. The operation unit 106 includes a keyboard and a pointing device (not shown) for entering an instruction and information by an operator.

The control unit 107 has a CPU (Central Processing Unit). The control unit 107 reads a control program stored in a not-shown storage and executes functions in the units in the ultrasonic image display apparatus 100.

Figure 3:
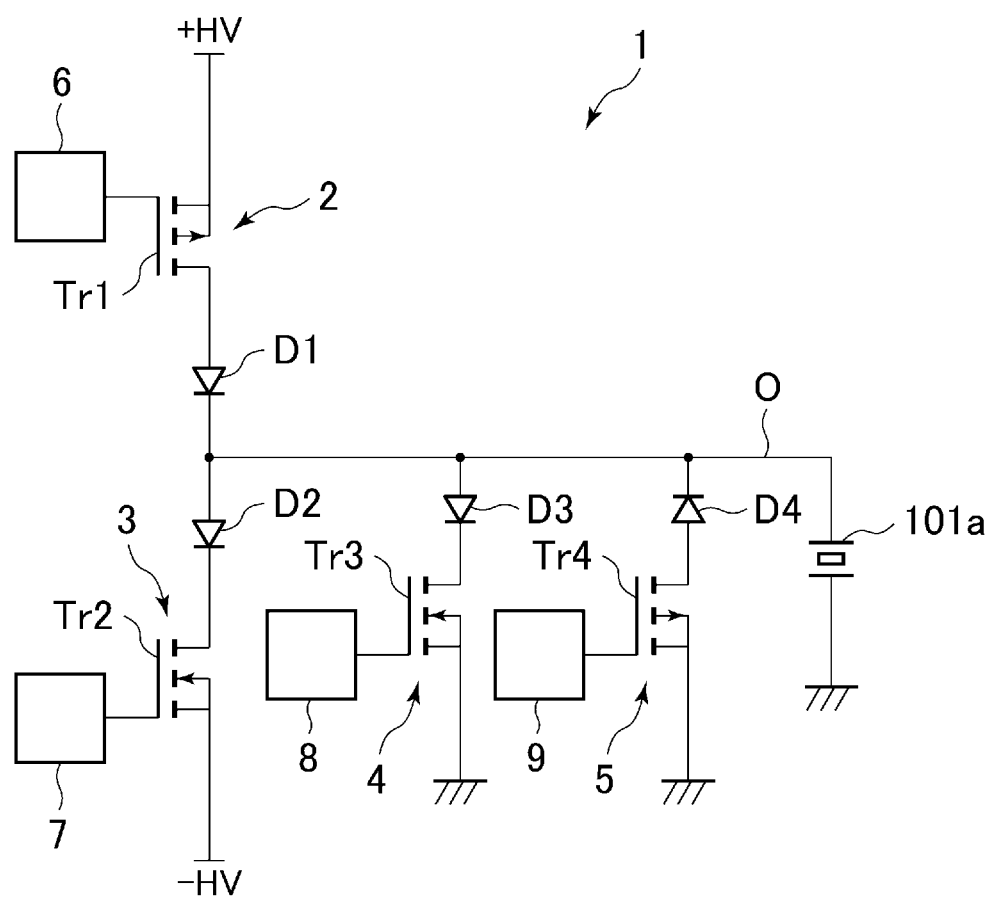
FIG. 3 is a circuit diagram showing an ultrasonic transducer drive circuit in the ultrasonic image display apparatus illustrated in FIG. 1.

Next, the ultrasonic transducer drive circuit 1 will be described with reference to FIG. 3. The ultrasonic transducer drive circuit 1 is provided for each ultrasonic transducer 101a (only one is shown in FIG. 3). The ultrasonic transducer driver circuit 1 outputs an electric signal for driving the ultrasonic transducer 101a to an output line O connected to the ultrasonic transducer 101a. In the embodiment, the electric signal is explained as voltage pulses made of a positive voltage pulse and a negative voltage pulse.

The ultrasonic transducer drive circuit 1 has a positive voltage supply circuit 2, a negative voltage supply circuit 3, a current-inflow-type ground clamp circuit 4, and a current-outflow-type ground clamp circuit 5. The positive voltage supply circuit 2, the negative voltage supply circuit 3, the current-inflow-type ground clamp circuit 4, and the current-outflow-type ground clamp circuit 5 are connected to the output line O.

The ultrasonic transducer 101a is equivalent to a circuit in which a capacitor and a resistor are connected in parallel.

The positive voltage supply circuit 2 is a circuit for supplying positive voltage to the output line O on the basis of a positive power supply voltage +HV and has a first transistor Tr1 and a first diode D1 provided between the first transistor Tr1 and the output line O. The first diode D1 is provided in a direction of passing current from the first transistor Tr1 to the output line O.

The first transistor Tr1 is a p-channel-type MOSFET (Metal-Oxide Semiconductor Field-Effect Transistor). In the first transistor Tr1, a power source for supplying the positive voltage +HV is connected to the source side, and the first diode D1 and the output line O are connected to the drain side. To the gate of the first transistor Tr1, a first driver circuit 6 outputting a drive signal to turn on/off the first transistor Tr1 is connected. The positive voltage supply circuit 2 enters an operation state when the first transistor Tr1 is in an on state and supplies the positive voltage to the output line O.

The positive voltage supply circuit 2 is an example of an embodiment of the positive voltage supply circuit. The first transistor Tr1 is an example of an embodiment of the first transistor. Further, the first driver circuit 6 is an example of an embodiment of the first driver circuit.

The negative voltage supply circuit 3 is a circuit for supplying the negative voltage to the output line O on the basis of a negative voltage –HV and has a second transistor Tr2 and a second diode D2 provided between the second transistor Tr2 and the output line O. The second diode D2 is provided in a direction of passing current from the output line O to the second transistor Tr2.

The second transistor Tr2 is an n-channel-type MOSFET. In the second transistor Tr2, a power source for supplying the negative voltage –HV is connected to the source side, and the second diode D2 and the output line O are connected to the drain side. To the gate of the second transistor Tr2, a second driver circuit 7 outputting a drive signal to turn on/off the second transistor Tr2 is connected. The negative voltage supply circuit 3 enters an operation state when the second transistor Tr2 is in an on state and supplies the negative voltage to the output line O.

The negative voltage supply circuit 3 is an example of an embodiment of the negative voltage supply circuit. The second transistor Tr2 is an example of an embodiment of the second transistor. Further, the second driver circuit 7 is an example of an embodiment of the second driver circuit.

The current-inflow-type ground clamp circuit 4 has a third transistor Tr3 and a third diode D3 provided between the third transistor Tr3 and the output line O. The third diode D3 is provided in a direction of passing current from the output line O to the third transistor Tr3. The current-inflow-type ground clamp circuit 4 is a circuit which enters an operation state when the third transistor Tr3 is in an on state and to which current flows in from the output line O, and is a circuit for changing the positive voltage in the output line O to the ground voltage.

The third transistor Tr3 is an n-channel-type MOSFET. In the third transistor Tr3, the third diode D3 and the output line O are connected to the drain side, and the source side is connected to the ground. To the gate of the third transistor Tr3, a third driver circuit 8 outputting a drive signal to turn on/off the third transistor Tr3 is connected.

The current-inflow-type ground clamp circuit 4 is an example of an embodiment of the current-inflow-type ground clamp circuit. The third transistor Tr3 is an example of an embodiment of the third transistor. Further, the third driver circuit 8 is an example of an embodiment of the third driver circuit.

The current-outflow-type ground clamp circuit 5 has a fourth transistor Tr4 and a fourth diode D4 provided between the fourth transistor Tr4 and the output line O. The fourth diode D4 is provided in a direction of passing current from the fourth transistor Tr4 to the output line O. The current-outflow-type ground clamp circuit 5 is a circuit which enters an operation state when the fourth transistor Tr4 is in an on state and current flows out to the output line O, and is a circuit for changing the negative voltage in the output line O to the ground voltage.

The fourth transistor Tr4 is a p-channel-type MOSFET. In the fourth transistor Tr4, the fourth diode D4 and the output line O are connected to the drain side, and the source side is connected to the ground. To the gate of the fourth transistor Tr4, a fourth driver circuit 9 outputting a drive signal to turn on/off the fourth transistor Tr4 is connected.

The current-outflow-type ground clamp circuit 5 is an example of an embodiment of the current-outflow-type ground clamp circuit. The fourth transistor Tr4 is an example of an embodiment of the fourth transistor. Further, the fourth driver circuit 9 is an example of an embodiment of the driver circuit.

Figure 4:
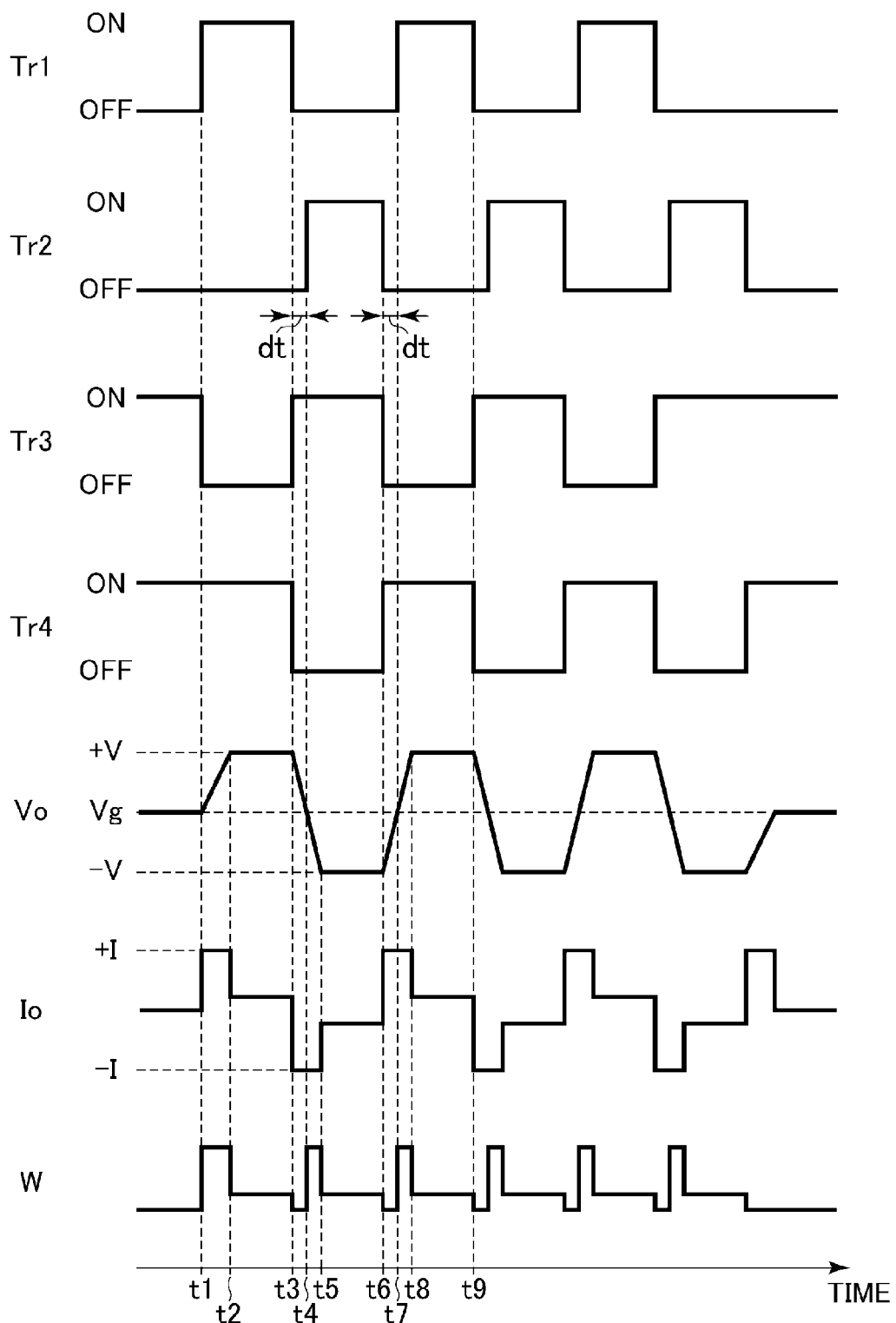
FIG. 4 is a diagram for explaining the operation of the ultrasonic transducer drive circuit shown in FIG. 3.

The operation of the ultrasonic transducer drive circuit 1 will now be described with reference to FIG. 4. First, at time t1, the first transistor Tr1 changes from the off state to the on state, and the third transistor Tr3 changes from the on state to the off state. At this time, the second transistor Tr2 remains in the off state, and the fourth transistor Tr4 remains in the on state.

When the first transistor Tr1 changes to the on state, output voltage Vo in the output line O rises from ground voltage Vg. At time t2 after lapse of predetermined time from the time t1, the output voltage Vo rises to positive voltage +V and, after that, is stabilized at the positive voltage +V.

Next, at time t3 after lapse of predetermined time from the time t2, the first transistor Tr1 changes from the on state to the off state, and the third transistor Tr3 changes from the off state to the on state. At time t3, the fourth transistor Tr4 changes from the on state to the off state.

When the third transistor Tr3 changes to the on state at time t3, the output voltage Vo starts decreasing from the positive voltage +V. At time t4 as a timing when the output voltage Vo changes to the ground voltage Vg, the second transistor Tr2 changes from the off state to the on state. Consequently, the output voltage Vo becomes negative and becomes negative voltage −V at time t5.

The time t4 as a timing when the second transistor Tr2 changes from the off state to the on state is time after lapse of predetermined delay time dt since the third transistor Tr3 changes from the off state to the on state. As the delay time dt, time required for the voltage in the output line to become the ground voltage Vg is preset.

The time t3 corresponds to time when a negative pulse is generated in a state where the voltage in the output line O is positive voltage.

The output voltage Vo becomes the negative voltage −V at time t5 and is stabilized. At time t6 after lapse of predetermined time since the time t5, the second transistor Tr2 changes from the on state to the off state, and the fourth transistor Tr4 changes from the off state to the on state. At time t6, the third transistor Tr3 changes from the on state to the off state.

By the change of the fourth transistor Tr4 to the on state at the time t6, the output voltage Vo starts rising from the negative voltage −V. At time t7 as a timing when the output voltage Vo becomes the ground voltage Vg, the first transistor Tr1 changes from the off state to the on state. As a result, the output voltage Vo becomes positive and becomes again positive voltage +V at time t8.

Time t7 as a timing when the first transistor Tr1 changes from the off state to the on state is time after lapse of predetermined delay time dt since the fourth transistor Tr4 changed from the off state to the on state. As the delay time dt, time required for the voltage in the output line O to become the ground voltage Vg is preset.

The time t6 corresponds to time when a positive pulse is generated in a state where the voltage in the output line O is negative voltage.

At time t9 after lapse of predetermined time from the time t8, the first transistor Tr1 changes again from the on state to the off state, and the third transistor Tr3 changes from the off state to the on state. At the time t9, the fourth transistor Tr4 changes from the on state to the off state.

The ultrasonic transducer drive circuit 1 repeats the above-described operation, thereby outputting pulses made of a positive pulse and a negative pulse to the output line O so that the ultrasonic transducers 101a drive. The pulse is a voltage pulse, the positive pulse is positive voltage pulse, and the negative pulse is negative voltage pulse.

Consumption of output current Io in the output line O and power W will be described with reference to FIGS. 5 to 9. It is assumed that the output current Io is current flowing in a part on the ultrasonic transducer 101a side more than the part in which the current-inflow-type ground clamp circuit 4 is connected and the part in which the current-outflow-type ground clamp circuit 5 is connected in the output line O.

FIGS. 5 to 9, the first transistor Tr1 to the fourth transistor Tr4 are simplified and shown as switches.

Figure 5:
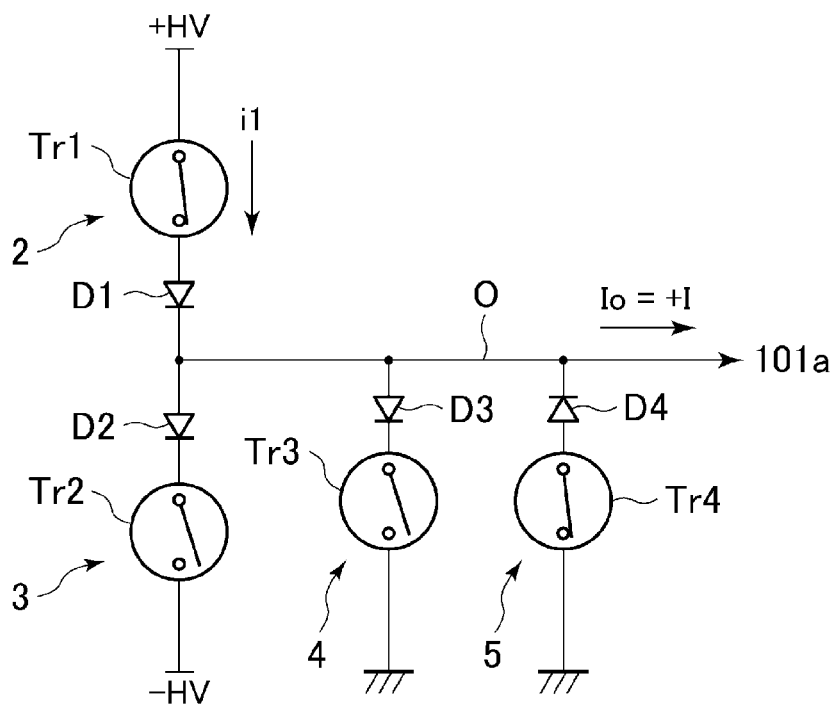
FIG. 5 is a diagram for explaining output current and power consumption from time t1 to time t2.

In a period from time t1 to time t2, as shown in FIG. 5, current i1 flows in the positive voltage supply circuit 2, and current +I flows as the output current Io. At this time, power W is consumed in the positive voltage supply circuit 2 (refer to FIG. 4).

Figure 6:
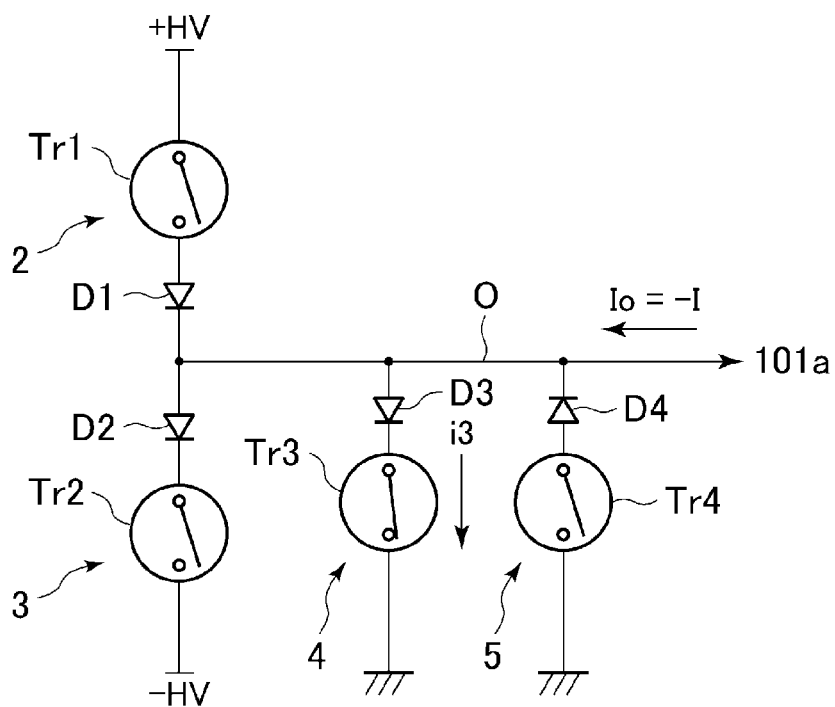
FIG. 6 is a diagram for explaining output current and power consumption from time t3 to time t4.

In a period from time t3 to time t4, as shown in FIG. 6, current i3 flows in the current-inflow-type ground clamp circuit 4, and current −I flows as the output current Io. At this time, since the second transistor Tr2 is in the off state, no current flows in the negative voltage supply circuit 3, and no power is consumed in the negative voltage supply circuit 3.

Figure 7:
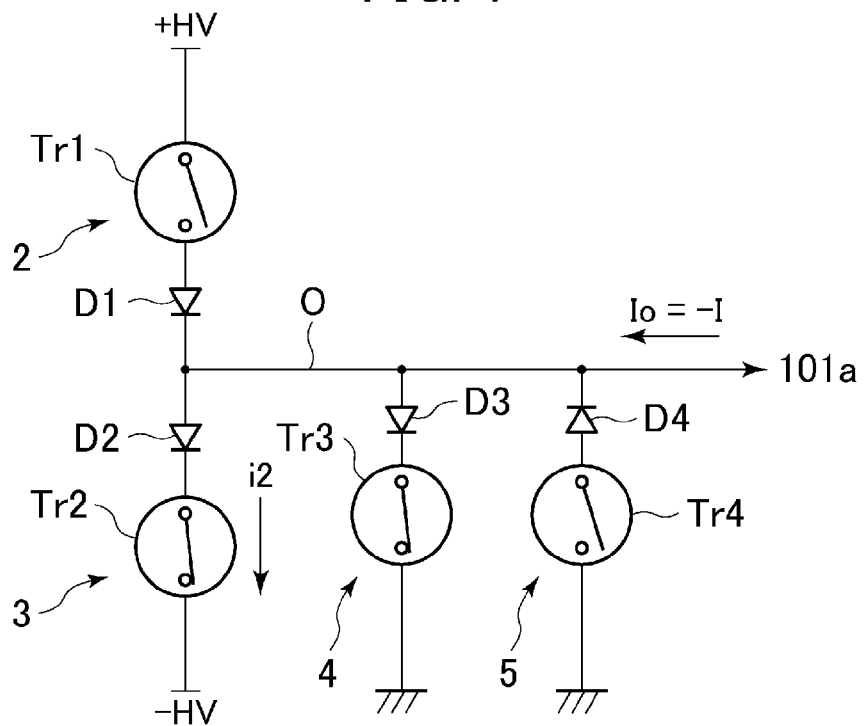
FIG. 7 is a diagram for explaining output current and power consumption from time t4 to time t5.

In a period from time t4 to time t5, as shown in FIG. 7, current i2 flows in the negative voltage supply circuit 3, and the current −I flows as the output current Io. At this time, the power W is consumed in the negative voltage supply circuit 3.

Figure 8:
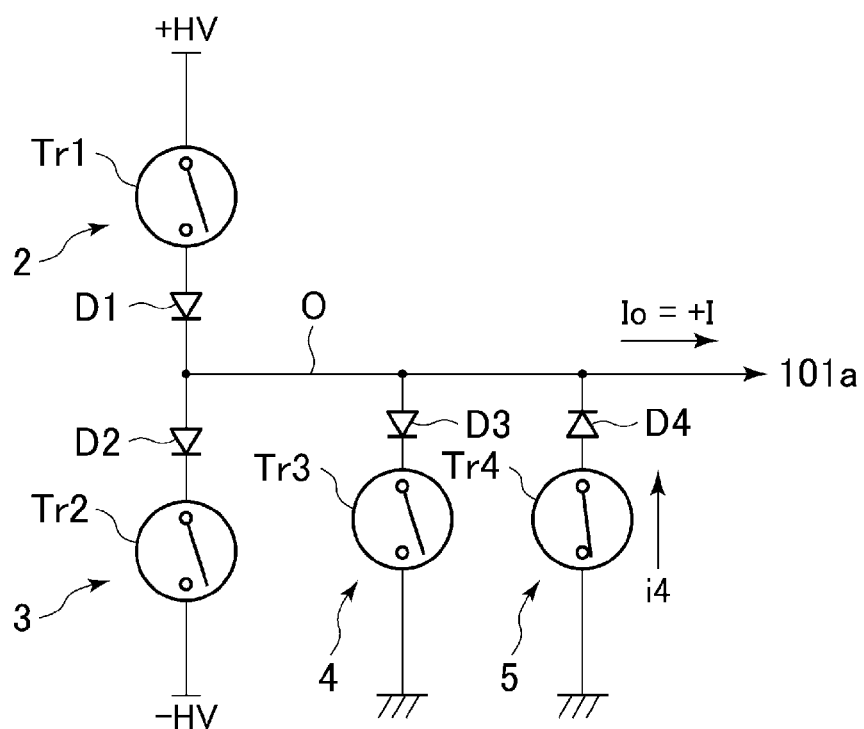
FIG. 8 is a diagram for explaining output current and power consumption from time t6 to time t7.

In a period from time t6 to time t7, as shown in FIG. 8, current i4 flows in the current-outflow-type ground clamp circuit 5, and the current +I flows as the output current Io. At this time, since the first transistor Tr1 is in the off state, no current flows in the positive voltage supply circuit 2, and no power is consumed in the positive voltage supply circuit 2.

Figure 9:
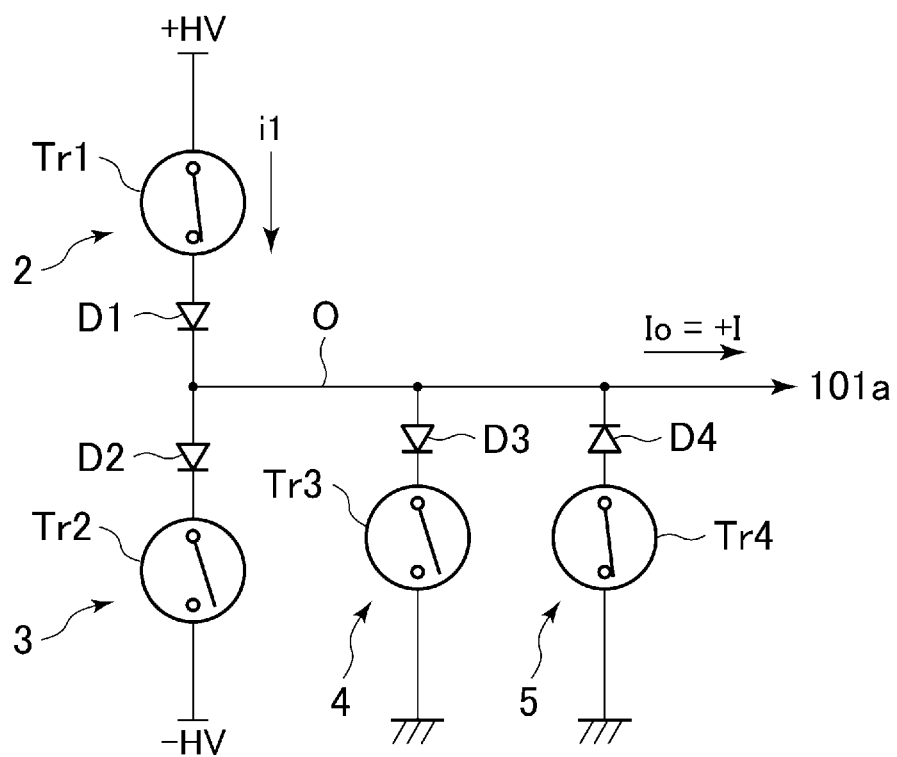
FIG. 9 is a diagram for explaining output current and power consumption from time t7 to time t8.

In a period from time t7 to time t8, as shown in FIG. 9, the current i1 flows in the positive voltage supply circuit 2, and the current +I flows as the output current Io. At this time, the power W is consumed in the positive voltage supply circuit 2.

In a period from time t2 to time t3 and a period from time t5 to time t6, current flows in a resistance component in the ultrasonic transducer 101a, current flows in the positive voltage supply circuit 2 and the negative voltage supply circuit 3 only by the amount of the current, and power is consumed.

To explain the fact that power consumption is suppressed more than the conventional technique by the ultrasonic transducer drive circuit 1 of the embodiment, the operation of a conventional ultrasonic transducer drive circuit will be described with reference to FIG. 10. The conventional ultrasonic transducer drive circuit has the same configuration as that of FIG. 3.

Only points different from the operation of the ultrasonic transducer drive circuit 1 of the embodiment will be described. First, at time t1, operation is similar to that of the ultrasonic transducer drive circuit 1 of the embodiment except that the transistor Tr4 changes from the on state to the off state. The transistors Tr3 and Tr4 continue in the off state since the time t1 and change to the on state at time t10 as the timing of changing the output voltage Vo to the ground voltage Vg.

At time t3, the first transistor Tr1 changes from the on state to the off state and the second transistor Tr2 changes from the off state to the on state. At time t6, the second transistor Tr2 changes from the on state to the off state, and the first transistor Tr1 changes from the off state to the on state.

Figure 10:
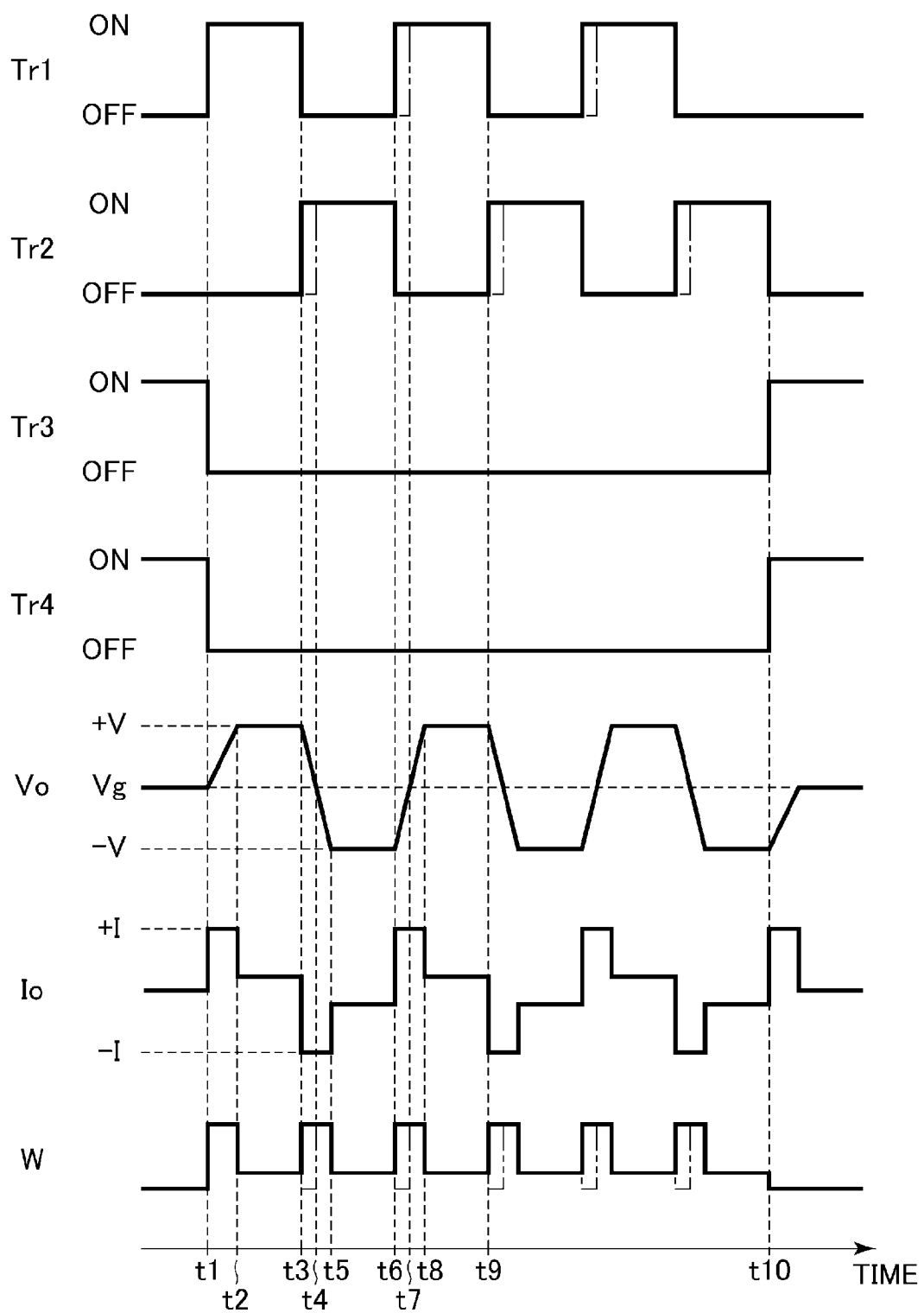
FIG. 10 is a diagram for explaining the operation of a conventional ultrasonic transducer drive circuit.

In FIG. 10, alternate long and two short dashes lines indicate the operation in the ultrasonic transducer drive circuit 1 of the embodiment.

Figure 11:
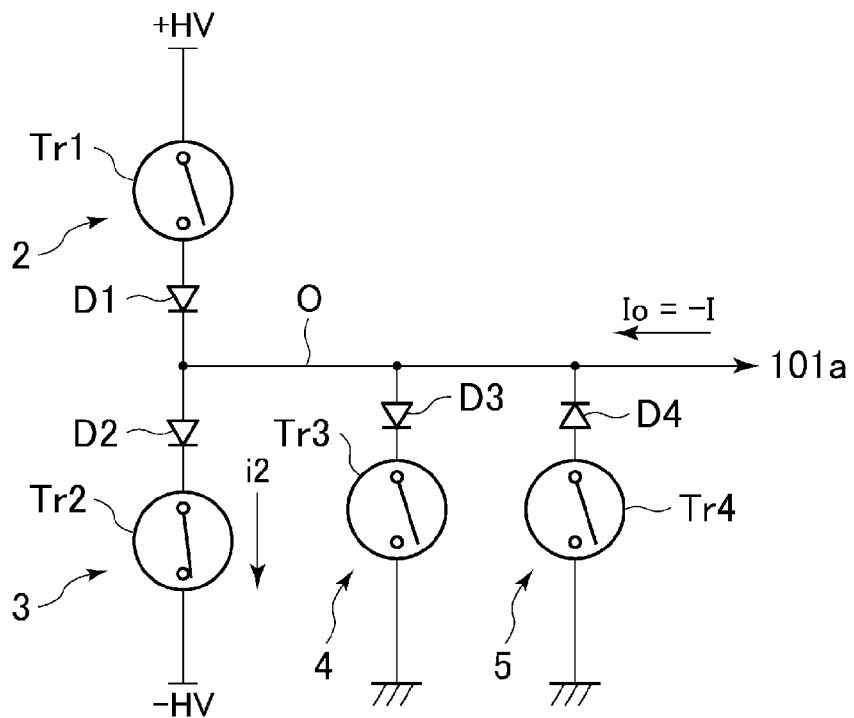
FIG. 11 is a diagram for explaining output current and power consumption from time t3 to time t4 in the conventional ultrasonic transducer drive circuit.

The output current Io and consumption of the power W in an output line O' in a conventional ultrasonic transducer drive circuit 1' performing such operation will be described with reference to FIGS. 11 and 12, particularly, in comparison to the embodiments described herein. In a period from time t3 to time t4, as shown in FIG. 11, current i2 flows in the negative voltage supply circuit 3, and the current −I flows as the output current Io. At this time, the power W is consumed in the negative voltage supply circuit 3.

Figure 12:
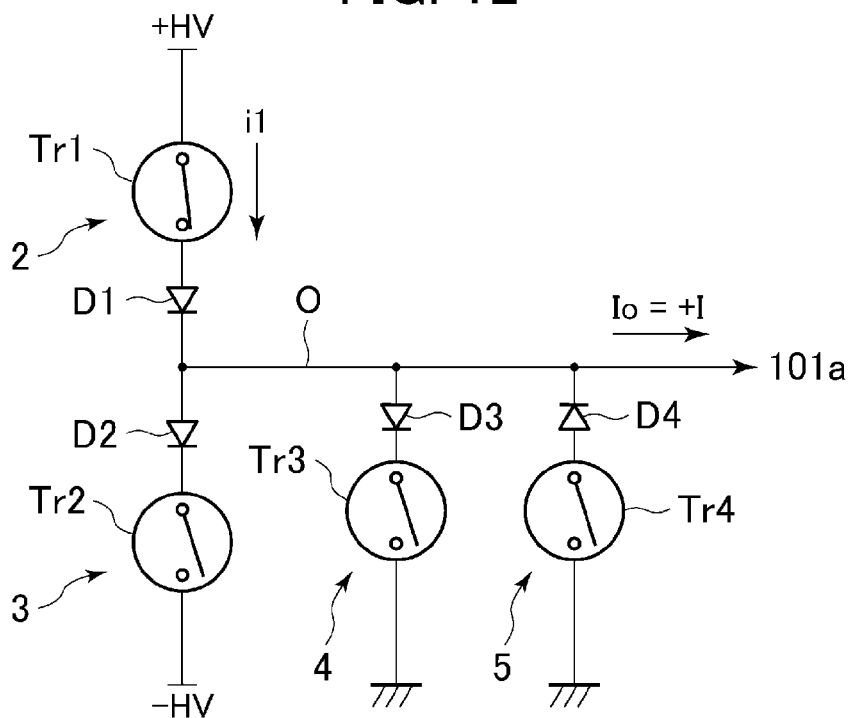
FIG. 12 is a diagram for explaining output current and power consumption from time t6 to time t7 in the conventional ultrasonic transducer drive circuit.

In the period from time t6 to time t7, as shown in FIG. 12, the current i1 flows in the positive voltage supply circuit 2 and the current +I flows as the output current Io. At this time, the power W is consumed in the positive voltage supply circuit 2.

On the other hand, in the ultrasonic transducer drive circuit 1 of the embodiment, at time t3 as time when the negative pulse is generated in a state where the voltage in the output line O is positive voltage, the third transistor Tr3 enters the on state. In the delay time dt from time t3 to time t4, the current-inflow-type ground clamp circuit 4 enters the operation state in place of the negative voltage supply circuit 3. The fourth transistor Tr4 enters the on state at time t6 when the positive pulse is generated in a state where the voltage in the output line O is negative voltage. In the delay time dt from time t6 to time t7, the current-outflow-type ground clamp circuit 4 operates in place of the positive voltage supply circuit 2. Therefore, in the ultrasonic transducer drive circuit 1 of the embodiment, in the period from time t3 to time t4 and the period from time t6 to time t7, no power is consumed in the positive voltage supply circuit 2 and the negative voltage supply circuit 3 (the alternate long and short dashes line in FIG. 10), so that the power consumption in the positive voltage supply circuit 2 and the negative voltage supply circuit 3 can be suppressed only by the amount more than the conventional technique.

Figure 13:
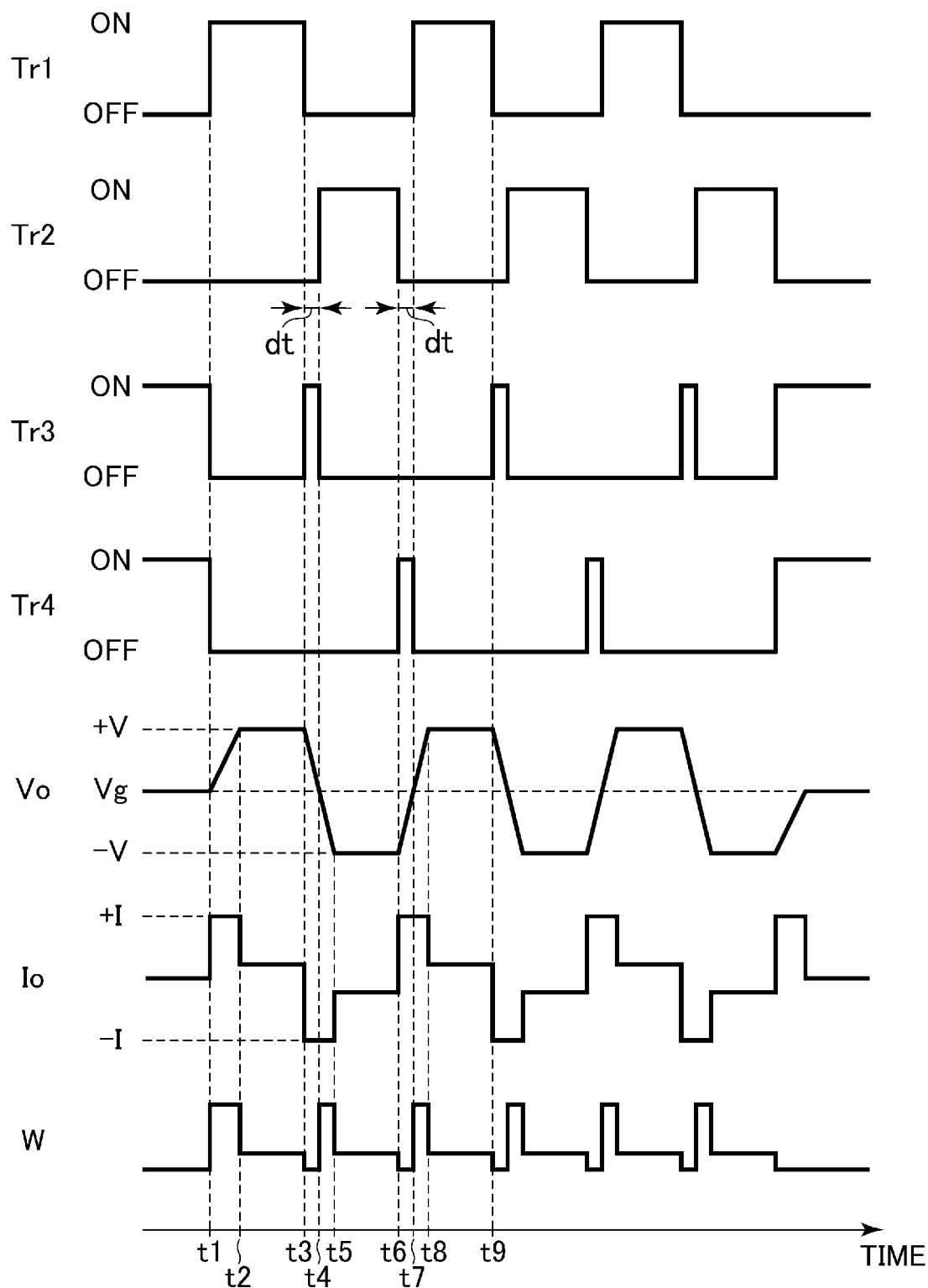
FIG. 13 is a diagram for explaining the operation of an ultrasonic transducer drive circuit in a first modification of the first embodiment.

Next, modifications of the first embodiment will be described. First, a first modification will be described with reference to FIG. 13. The third transistor Tr3 does not have to be in the on state to the time t6 but may be in the on state until at least time t4, that is, until the positive voltage in the output line O becomes the ground voltage Vg. The fourth transistor Tr4 does not have to be in the on state till time t9 but may be in the on state until at least time t7, that is, until the negative voltage in the output line O becomes the ground voltage Vg.

The transistor Tr4 may change from the on state to the off state at the time t1.

Figure 14:
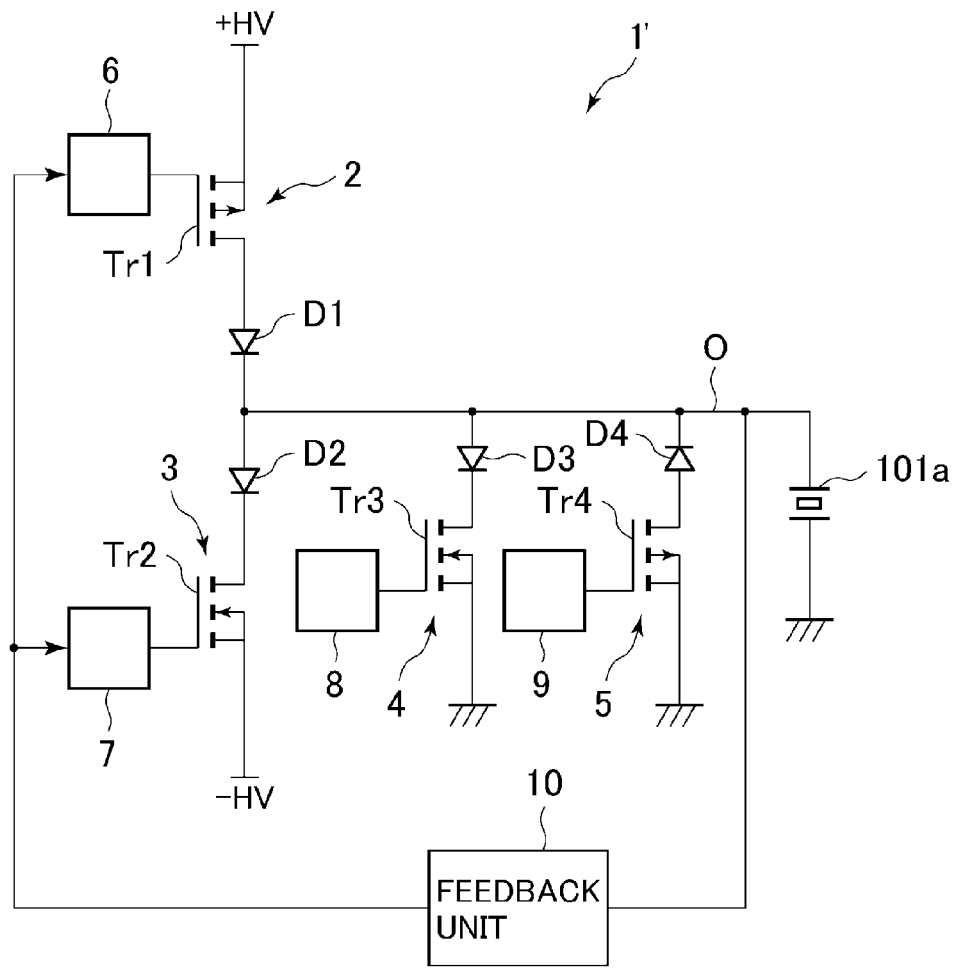
FIG. 14 is a circuit diagram showing an ultrasonic transducer drive circuit in a second modification of the first embodiment.

A second modification will now be described. In the second modification, the delay time dt is not preset but is determined on the basis of the output voltage Vo. Concretely, as shown in FIG. 14, the ultrasonic transducer drive circuit 1' of the second modification has a feedback unit 10. The input side of the feedback unit 10 is connected to the output line O. The output side of the feedback unit 10 is connected to the first driver circuit 6 and the second driver circuit 7.

Figure 15:
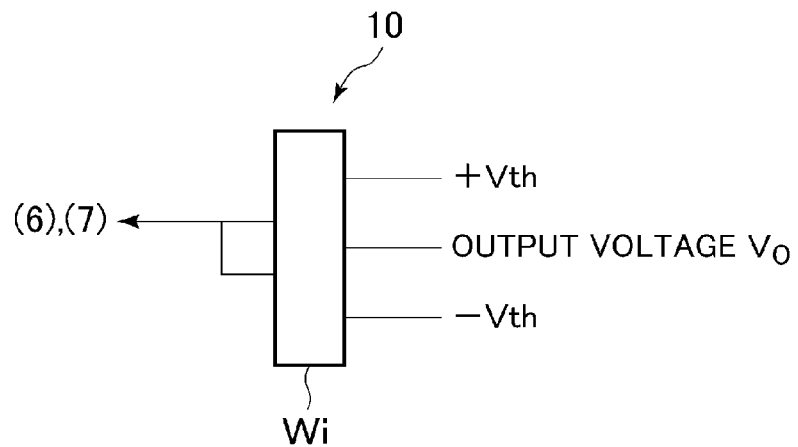
FIG. 15 is a diagram showing the configuration of a feedback unit illustrated in FIG. 14.

The feedback unit 10 is constructed by a window comparator Wi shown in FIG. 15. To the window comparator Wi, the output voltage Vo of the output line O is supplied. The window comparator Wi compares the output voltage Vo with a positive threshold voltage +Vth and a negative threshold voltage −Vth and outputs a signal to the first driver circuit 6 and the second driver circuit 7.

The range of the negative threshold voltage −Vth or higher and the positive threshold voltage +Vth or lower includes the ground voltage Vg, and is an example of the embodiment of the voltage in the predetermined range.

Figure 16:
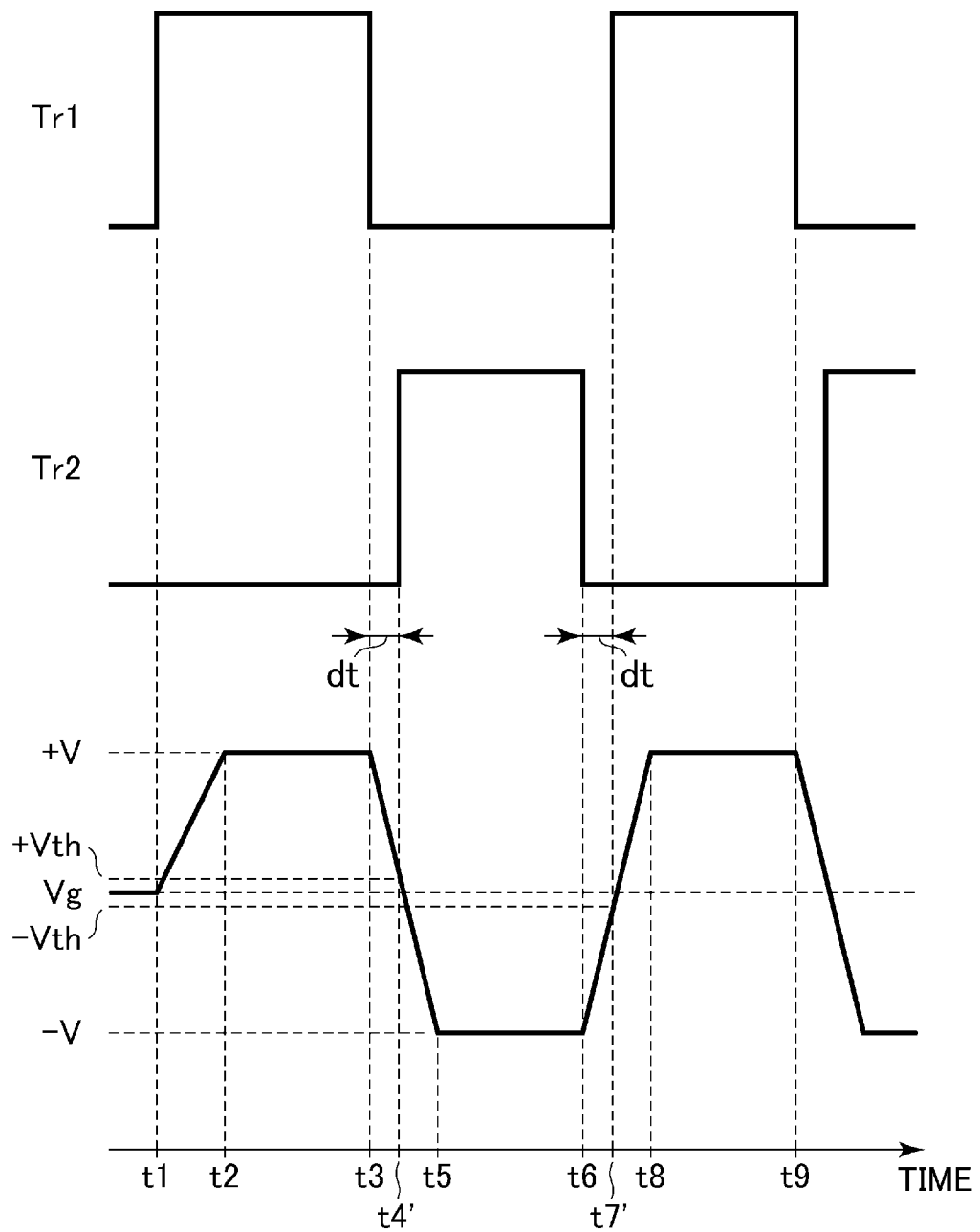
FIG. 16 is a diagram for explaining the operation of the ultrasonic transducer drive circuit in the second modification of the first embodiment.

The operation of the second modification will be described with reference to FIG. 16. Points different from the foregoing embodiment with respect to the operations of the first transistor Tr1 and the second transistor Tr2 will be described. The operations of the third transistor Tr3 and the fourth transistor Tr4 are the same as those of the foregoing embodiment, so that the description will not be repeated.

At time t3, the output voltage Vo starts decreasing from the positive voltage +V. When the output voltage Vo becomes the positive threshold voltage +Vth at time t4', the feedback unit 10 outputs a signal which makes the second transistor Tr2 enter the on state to the second driver circuit 7. By the signal, the second transistor Tr2 is turned on. As described above, the output voltage Vo becomes close to the ground voltage Vg from the positive voltage +V, the second transistor Tr2 changes from the off state to the on state, so that the output voltage Vo becomes negative voltage.

When the output voltage Vo starts rising from the negative voltage −V at time t6 and becomes the negative threshold voltage −Vth at time t7', the feedback unit 10 outputs a signal which makes the first transistor Tr1 enter the on state to the first driver circuit 6. By the signal, the first transistor Tr1 is turned on. As described above, the output voltage Vo becomes close to the ground voltage Vg from the negative voltage −V, the first transistor Tr1 changes from the off state to the on state, so that the output voltage Vo becomes positive voltage.

Also in the second modification, as the delay time dt, time from the time t3 to time t4' or time from time t6 to time t7' is assured, and the power consumption can be suppressed more than the conventional technique.

Second Embodiment

Next, a second embodiment will be described. The ultrasonic transducer drive circuit 1 of the second embodiment has the same configuration as that of FIG. 4, and operations different from those of the first embodiment will be described now.

Figure 17:
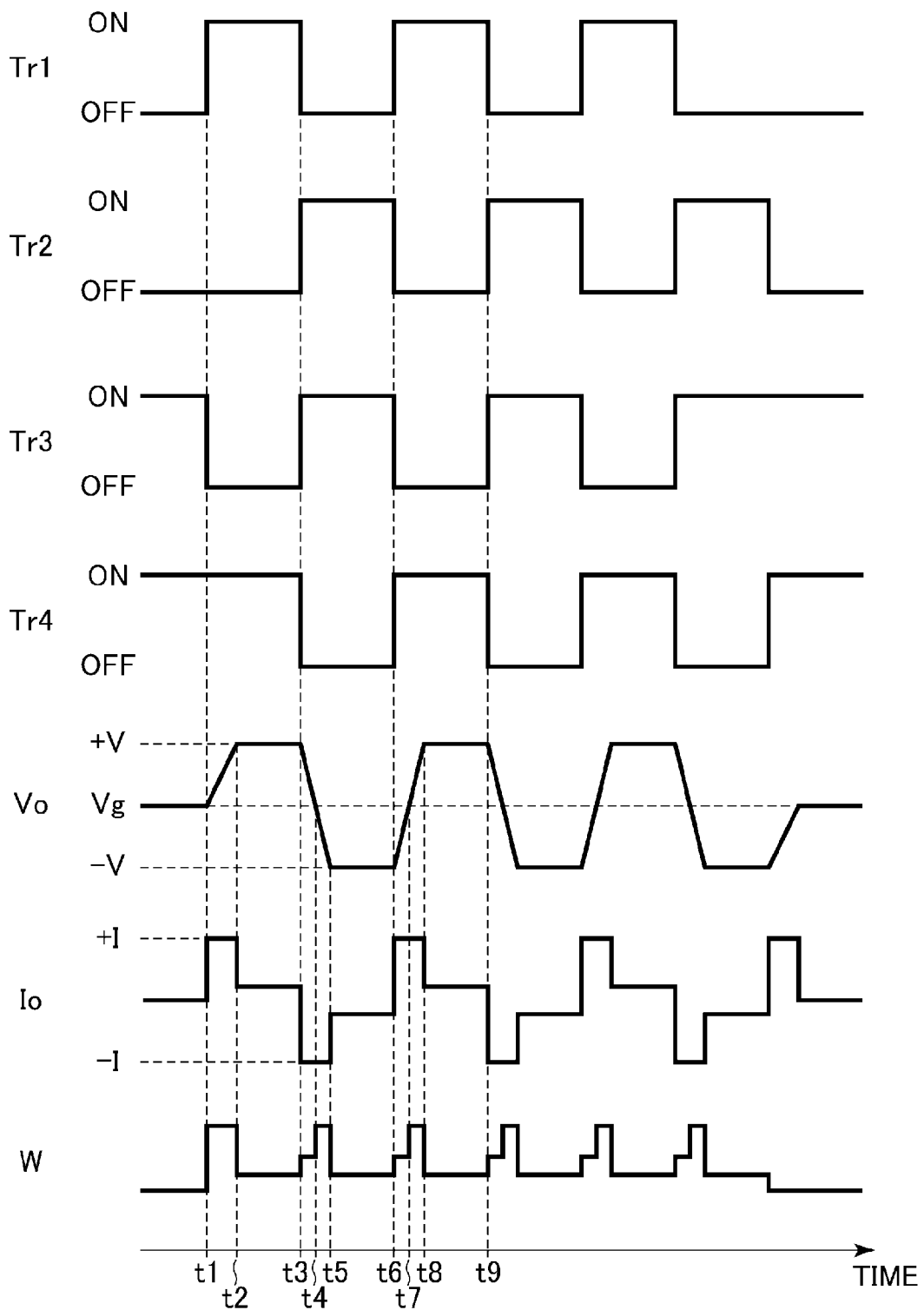
FIG. 17 is a diagram for explaining the operation of an ultrasonic transducer drive circuit in a second embodiment.

In the ultrasonic transducer drive circuit 1 of the embodiment, as shown in FIG. 17, the second transistor Tr2 changes from the off state to the on state at time t3. At time t6, the first transistor Tr1 changes from the off state to the on state. That is, in the embodiment, there is no delay time dt.

In the ultrasonic transducer drive circuit 1 of the embodiment, different from the first embodiment, when the third transistor Tr3 changes from the off state to the on state, the second transistor Tr2 changes from the off state to the on state. When the fourth transistor Tr4 changes from the off state to the on state, the first transistor Tr1 changes from the off state to the on state. Also in such an ultrasonic transducer drive circuit 1 of the embodiment, the power consumption can be suppressed more than the conventional technique. The consumption of the power W will now be described with reference to FIGS. 18 and 19.

Figure 18:
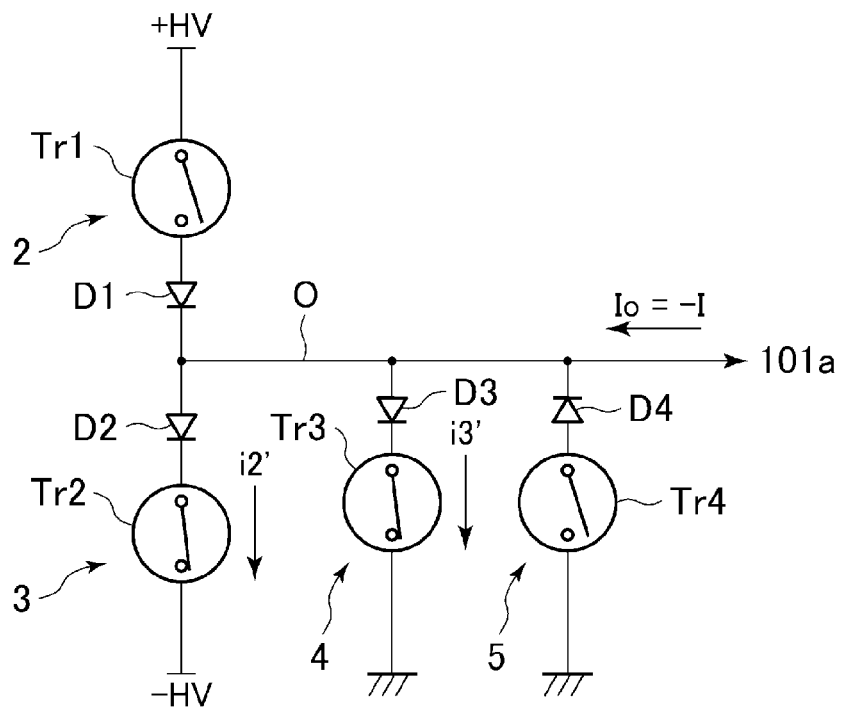
FIG. 18 is a diagram for explaining the flow of current from time t3 to time t4 in the ultrasonic transducer drive circuit of the second embodiment.

When the second transistor Tr2 and the third transistor Tr3 enter the on state at time t3, as shown in FIG. 18, current i2' flows in the negative voltage supply circuit 3, current i3' flows in the current-inflow-type ground clamp circuit 4, and current −I flows as the output current Io.

In the conventional ultrasonic transducer drive circuit 1', in the period from time t3 to time t4, as shown in FIG. 11, although the current i2 flows in the negative voltage supply circuit 3, no current flows in the current-inflow-type ground clamp circuit 4. On the other hand, in the ultrasonic transducer drive circuit 1, current i3' flows also in the current-inflow-type ground clamp circuit 4, and the output current Io is split. Consequently, the current i2' becomes smaller than the current i2 (i2'<i2).

Figure 19:
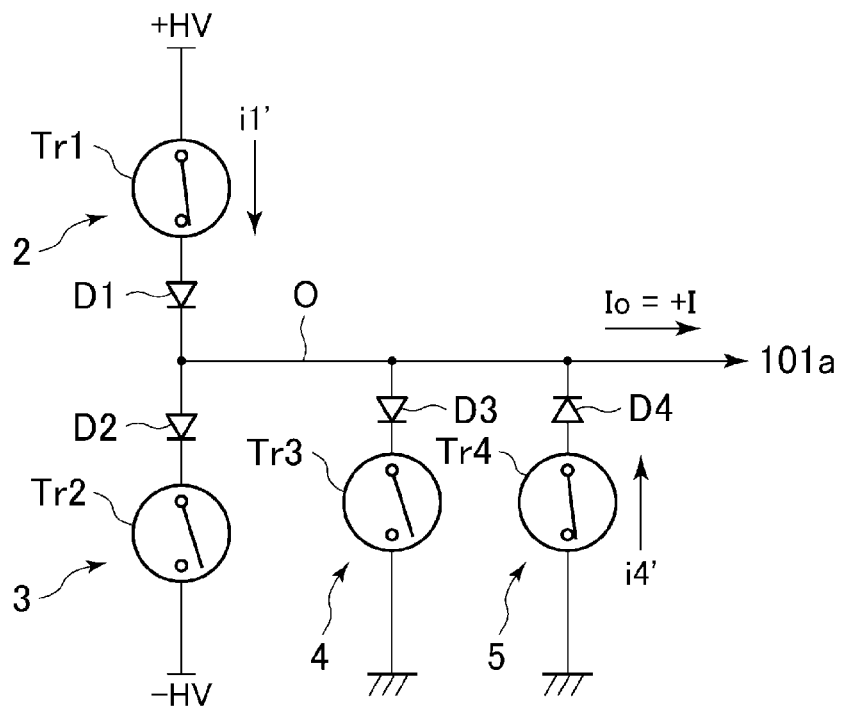
FIG. 19 is a diagram for explaining the flow of current from time t6 to time t7 in the ultrasonic transducer drive circuit of the second embodiment.

When the first transistor Tr1 and the fourth transistor Tr4 enter the on state at time t6, as shown in FIG. 19, the current i1' flows in the positive voltage supply circuit 2, the current i4' flows in the current-outflow-type ground clamp circuit 5, and the current +I flows as the output current Io.

In the conventional ultrasonic transducer drive circuit 1', in the period from time t6 to time t7, as shown in FIG. 12, although the current i1 flows in the positive voltage supply circuit 2, no current flows in the current-outflow-type ground clamp circuit 5. On the other hand, in the ultrasonic transducer drive circuit 1, the size of the output current Io is the same as that in the conventional ultrasonic transducer drive circuit 1'. Consequently, the current i1' becomes smaller than the current i1 (i1'<i1) only by the amount of the current i4' flowing in the current-outflow-type ground clamp circuit 5.

As described above, in the ultrasonic transducer drive circuit 1, during the period from time t3 to time t4 and the period from time t6 to time t7, the current flowing in the positive voltage supply circuit 2 and the negative voltage supply circuit 3 can be reduced as compared with that in the conventional technique. Thus, the power consumption in the positive voltage supply circuit 2 and the negative voltage supply circuit 3 can be suppressed more than that in the conventional technique.

Although the present invention has been described by the foregoing embodiments, obviously, the invention can be modified without changing the gist of the present invention. For example, each of the ultrasonic transducer drive circuits 1 and 1' may be provided in the ultrasonic probe 101.

The invention claimed is:

1. An ultrasonic transducer drive circuit for driving an ultrasonic transducer by outputting pulses including a positive pulse and a negative pulse to an output line coupled to the ultrasonic transducer, the ultrasonic transducer drive circuit comprising:
a positive voltage supply circuit configured to supply positive voltage to the output line;
a negative voltage supply circuit configured to supply negative voltage to the output line;
a current-inflow-type ground clamp circuit configured to operate when voltage in the output line is positive voltage, and configured to change the voltage in the output line to ground voltage; and
a current-outflow-type ground clamp circuit configured to operate when voltage in the output line is negative voltage, and configured to change the voltage in the output line to ground voltage,
wherein the current-inflow-type ground clamp circuit is configured to enter an operation state at a time of generating the negative pulse in a state where the voltage in the output line is positive voltage;
the current-outflow-type ground clamp circuit is configured to enter an operation state at a time of generating the positive pulse in a state where the voltage in the output line is negative voltage;
the positive voltage supply circuit is configured to start operation after a first predetermined delay time that lasts from an operation start point of the current-outflow-type ground clamp circuit until the voltage in the output line becomes ground voltage; and
the negative voltage supply circuit is configured to start operation after a second predetermined delay time that lasts from an operation start point of the current-inflow-type ground clamp circuit until the voltage in the output line becomes ground voltage.

2. The ultrasonic transducer drive circuit according to claim 1, wherein the current-inflow-type ground clamp circuit is configured to operate at least until the positive voltage in the output line becomes ground voltage, and the current-outflow-type ground clamp circuit is configured to operate at least until the negative voltage in the output line becomes ground voltage.

3. An ultrasonic transducer drive circuit for driving an ultrasonic transducer by outputting pulses including a positive pulse and a negative pulse to an output line coupled to the ultrasonic transducer, the ultrasonic transducer drive circuit comprising:
a positive voltage supply circuit configured to supply positive voltage to the output line;
a negative voltage supply circuit configured to supply negative voltage to the output line;
a current-inflow-type ground clamp circuit configured to operate when voltage in the output line is positive voltage, and configured to change the voltage in the output line to ground voltage; and
a current-outflow-type ground clamp circuit configured to operate when voltage in the output line is negative voltage, and configured to change the voltage in the output line to ground voltage,
wherein the current-inflow-type ground clamp circuit is configured to enter an operation state at a time of generating the negative pulse in a state where the voltage in the output line is positive voltage;
the current-outflow-type ground clamp circuit is configured to enter an operation state at a time of generating the positive pulse in a state where the voltage in the output line is negative voltage;
the positive voltage supply circuit is configured to start operation after a first predetermined delay time that lasts from an operation start point of the current-outflow-type ground clamp circuit until the voltage in the output line becomes a voltage in a first predetermined range that includes ground voltage; and
the negative voltage supply circuit is configured to start operation after a second predetermined delay time that lasts from an operation start point of the current-inflow-type ground clamp circuit until the voltage in the output line becomes a voltage in a second predetermined range that includes ground voltage.

4. An ultrasonic transducer drive circuit for driving an ultrasonic transducer by outputting pulses including a positive pulse and a negative pulse to an output line coupled to the ultrasonic transducer, the ultrasonic transducer drive circuit comprising:
a positive voltage supply circuit configured to supply positive voltage to the output line;
a negative voltage supply circuit configured to supply negative voltage to the output line;
a current-inflow-type ground clamp circuit configured to operate when voltage in the output line is positive voltage, and configured to change the voltage in the output line to ground voltage; and a current-outflow-type ground clamp circuit configured to operate when voltage in the output line is negative voltage, and configured to change the voltage in the output line to ground voltage, wherein the positive voltage supply circuit is configured to start operation at the same time as the operation start of the current-outflow-type ground clamp circuit; and the negative voltage supply circuit is configured to start operation at the same time as the operation start of the current-inflow-type ground clamp circuit.

5. The ultrasonic transducer drive circuit according to claim 1, wherein the positive voltage supply circuit includes a first transistor configured to start and stop supply of the positive voltage to the output line.

6. The ultrasonic transducer drive circuit according to claim 5, wherein the operation start timing of the current-inflow-type ground clamp circuit is a timing when the first transistor changes from an on state to an off state.

7. The ultrasonic transducer drive circuit according to claim 5, further comprising a first driver circuit configured to drive the first transistor.

8. The ultrasonic transducer drive circuit according to claim 1, wherein the negative voltage supply circuit includes a second transistor configured to start and stop supply of negative voltage to the output line.

9. The ultrasonic transducer drive circuit according to claim 8, wherein the operation start timing of the current-outflow-type ground clamp circuit is a timing when the second transistor changes from an on state to an off state.

10. The ultrasonic transducer drive circuit according to claim 8, further comprising a second driver circuit configured to drive the second transistor.

11. The ultrasonic transducer drive circuit according to claim 1, wherein the current-inflow-type ground clamp circuit includes a third transistor connected between the output line and the ground such that when the third transistor is in an on state, current flows in from the output line.

12. The ultrasonic transducer drive circuit according to claim 11, further comprising a third driver circuit configured to drive the third transistor.

13. The ultrasonic transducer drive circuit according to claim 1, wherein the current-outflow-type ground clamp circuit includes a fourth transistor connected between the output line and the ground such that when the fourth transistor is in an on state, current is passed to the output line.

14. The ultrasonic transducer drive circuit according to claim 13, further comprising a fourth driver circuit configured to drive the fourth transistor.

15. The ultrasonic transducer drive circuit according to claim 1, wherein the pulses are voltage pulses.

* * * * *